United States Patent
Mari et al.

(10) Patent No.: US 7,524,425 B2
(45) Date of Patent: Apr. 28, 2009

(54) FILTER FOR THE REMOVAL OF SUBSTANCES FROM BLOOD PRODUCTS

(75) Inventors: Giorgio Mari, Mirandola (IT); Stefano Veronesi, S. Giacomo Mirandola (IT); Bernd Mathieu, Spiesen (DE)

(73) Assignee: Fresenius Hemocare Italia S.r.l., Cavezzo (Modena) (IT)

( * ) Notice: Subject to any disclaimer, the term of this patent is extended or adjusted under 35 U.S.C. 154(b) by 581 days.

(21) Appl. No.: 10/573,175

(22) PCT Filed: Sep. 22, 2004

(86) PCT No.: PCT/EP2004/010618

§ 371 (c)(1),
(2), (4) Date: Mar. 23, 2006

(87) PCT Pub. No.: WO2005/028003

PCT Pub. Date: Mar. 31, 2005

(65) Prior Publication Data

US 2008/0230475 A1  Sep. 25, 2008

(30) Foreign Application Priority Data

Sep. 23, 2003  (EP) .................. 03021435

(51) Int. Cl.
*B01D 29/00* (2006.01)
*B01D 37/00* (2006.01)
*B01D 39/00* (2006.01)

(52) U.S. Cl. .................. 210/767; 210/252; 210/257.1; 210/483; 210/488; 210/489; 210/490; 210/500.27; 210/500.34; 210/500.35; 210/500.36; 210/500.38; 210/500.42; 210/503; 210/504; 210/505; 210/506; 210/508

(58) Field of Classification Search .................. 210/252, 210/257.1, 483, 488, 489, 490, 500.27, 500.34, 210/500.35, 500.36, 500.38, 500.42, 503, 210/504, 505, 506, 508, 767
See application file for complete search history.

(56) References Cited

U.S. PATENT DOCUMENTS

| 4,618,533 | A | 10/1986 | Steuck | 428/315 |
| 5,454,946 | A | 10/1995 | Heagle et al. | 210/503 |
| 5,580,465 | A | 12/1996 | Pall et al. | 210/767 |
| 5,660,731 | A | 8/1997 | Piechocki et al. | 210/669 |
| 6,159,375 | A | 12/2000 | Lee et al. | 210/645 |
| 6,337,026 | B1 | 1/2002 | Lee et al. | 210/767 |
| 6,951,713 | B2 * | 10/2005 | Hei et al. | 435/2 |
| 2001/0009756 | A1 | 7/2001 | Hei et al. | 435/2 |

FOREIGN PATENT DOCUMENTS

| EP | 0313348 A2 | 4/1989 |
| EP | 0397403 A1 | 11/1990 |

\* cited by examiner

*Primary Examiner*—John Kim
(74) *Attorney, Agent, or Firm*—Jacobson Holman PLLC

(57) ABSTRACT

A filter device for the depletion of the leukocyte content from blood products comprising: a porous element comprising at least one fibrous web having a pore size suitable for leukocyte removal (possibly the range for the pore size should be defined), said web comprising fibres of a hydrophobic polymer coated with a hydrophilic polymer suitable to enhance the CWST of said hydrophobic polymer, characterised in that said web further includes adsorbent particles having a mean diameter lower than 30 µm, said particles being bonded to said fibres by means of said hydrophilic polymer coating said fibres.

11 Claims, No Drawings

FILTER FOR THE REMOVAL OF SUBSTANCES FROM BLOOD PRODUCTS

This is a nationalization of PCT/EP2004/010618 filed 22 Sep. 2004 and published in English.

The present invention relates to a filter for the removal of leukocytes from blood or blood components and more particularly, to a leukocyte filter adapted for use in the blood purification devices, such as blood bag systems which are conventionally used for the separation of whole blood into leukocyte depleted hemocomponents.

The blood filters, to which the present invention relates, typically comprise a housing with inlet and outlet ports and at least a porous element, within the housing, interposed between the inlet and outlet port.

The porous element usually consists of a web which may be formed by one or more layers of filtering material, typically a non-woven fabric.

According to the prior art, the porous elements can be produced from any material compatible with blood, which is capable of forming fibres including natural or synthetic fibres.

The preferred materials are synthetic polymers, such as particularly polyolefins, polyesters and polyamides.

Fibrous leukocyte filters are well-known in the prior art and are described e.g. in EP-A-0 313 348 and EP-A-0 397 403.

Preferred materials for use in leukocyte filters are synthetic resins, which are adapted to be processed into very fine fibres (with a diameter preferably lower than 3 μm) by melt-blowing.

The currently used preferred material is polybutyleneterephthalate (PBT). The surface properties of the employed fibre material can be modified to increase its wettability or its Critical Wetting Surface Tension (CWST), which is a measure Critical Wetting Surface Tension (CWST), which is a measure of the hydrophilicity of the material.

To this end, fibres of a hydrophobic resin, such as PBT, have been coated with a more hydrophilic polymer, such as particularly hydrophilic acrylic polymers or copolymers or hydrophilic polyurethanes.

The polymeric material used for the fibres can also be rendered more hydrophilic by surface grafting the polymeric material, particularly PBT, with compounds containing an ethylenically unsaturated group, such as an acrylic moiety combined with hydroxyl groups or methylacrylate or methylmethacrylate and combinations thereof, as described in EP-A-0 313 348.

In general, a filter with a higher hydrophilicity is enhancing the recovery of platelets, as described in U.S. Pat. No. 5,580,465 and U.S. Pat. No. 4,618,533.

Also known in the art are composite leukocyte filters comprising polymeric fibres and solid particles to increase the total surface area of the filtering material.

U.S. Pat. No. 5,454,946 describes a filter material for filtering leukocytes comprising a web made by interlocked matrix fibres, mainly consisting of glass fibres and fibrillated particles of textile fibre material disposed within the spaces of the matrix. A thermoplastic binder is disposed at the crossover portion of the matrix fibres. The fibrillated particles do not have adsorption properties and are not porous in nature.

U.S. Pat. No. 6,337,026 also describes filtration media for leukocyte depletion of the type described in U.S. Pat. No. 5,454,946 wherein the particles have a very high specific surface area of at least 100 m$^2$/g and the weight ratio of the particles to the matrix fibres is less than 100.

US 2001/00 09756 A1 describes a device for reducing the concentration of low molecular weight compounds in biological composition comprising an inert matrix containing adsorbent particles. The compounds which can be removed, which have molecular weight from 100 g/mol to about 30000 g/mol include pathogen-inactivating agents such as photoactivation products, aminoacridines, organic dyes and phenothiazines. Such devices are not described for use in leukocyte depletion.

The present invention provides a filtering material and filter devices which in addition to being able to remove low molecular weight compounds from blood products and whole blood or blood components also achieve high efficiency in leukocyte removal.

The subject matter of the invention is defined in the appended claims.

The filter device, which constitute a subject of the invention, has a porous element comprising at least one fibrous web having a pore size suitable for leukocyte removal. The said web comprises fibres of a hydrophobic polymer which are at least partially coated with a hydrophilic polymer suitable to increase the Critical Wetting Surface Tension (CWST) or hydrophilicity of said hydrophobic polymer. Suitable hydrophobic polymers include polyolefins, such as polyethylene and polypropylene, polyamides, polyaramides, polyacrylics, polyacrilonitriles, cellulose acetate, polyvinylidenefluoride and polyesters. The preferred polymer is polybutylenterephthalate (PBT).

The fibre diameter of the non woven web is generally in the range of from 0.01 micron to 5 micron.

The preferred technique for producing the fibres of the non woven random web is by melt blowing technology. By that technology, the intrinsic porosity and the fibre diameter distribution of the fabric can be determined by the process parameters such as spinneret characteristics and setting, D.C.D. (Distance Conveyor to Die), hot air and polymer throughput, process temperature, suction and positioning (e.g. inclination) of the collector.

The adsorbent particles are bonded to the fibre matrix so that they are not released under either static or flow conditions in contact with biologic fluids. Adsorbent microparticles for use in the filter of the invention include microparticles made of a biocompatible material or at least partially coated with a biocompatible material. Adsorbent particles or beads, suitable for removing toxicants from blood or plasma are known in the art. They include polymeric materials such as polyacrylics, polyesters, polyamides, polyacrylamides and polystyrene copolymers; a preferred material is polystyrenedivinylbenzene (DVB) or polyamide. Also active charcoal could be used. The particles or beads diameter may vary in a wide range generally of from 0.1 to 200 micron. However, it is particularly preferred the use of particles having a mean diameter lower than 30 μm. Also contemplated within the scope of the invention is the use of microparticles having an internal microporosity with a specific surface area higher than 200 m$^2$/g up to about 800 m$^2$/g or more.

The hydrophilic polymer which is used to enhance the hydrophilicity of the hydrophobic fibres is preferably selected from co-polymers obtained by polymerization of vinylacetate (VA) and vynilpyrrolidone (VP) in a different mole ratio, such as VA/VP=50÷4.

The adsorbent particles may be bonded to the fibre surface by means of several methods known in the art e.g. by heat treatment, inclusion methods and coating. However, according to the invention, the preferred method is by coating with the use of the same hydrophilic polymer which is used to enhance the hydrophilicity of the fibre material. According to the preferred method a porous web of hydrophobic fibres (preferably PBT) is impregnated or soaked with a solution of the selected hydrophilic polymer, including a solvent for the said polymer (e.g. an alcoholic solvent) solvent and in suspension said adsorbent particles. By properly selecting the concentration of the hydrophilic polymer in the solution and the amount of particles in the solution it is possible to achieve, upon drying of the thus impregnating web, a filtering material wherein the adsorbent particles are bonded to the fibre surface and the fibre surface as well as the particle surface is at least partially coated with the hydrophilic polymer. It as been found that such a coating does not impair the adsorption properties of the adsorbent particles. In this method, preferably, the hydrophilic polymer, which as stated before is preferably polyvinylpyrrolidone, is used in the impregnating solution with a concentration of from 0.1 to 5% by weight and the adsorbent particles, which are preferably made of polystyrene-DVB or polyamide are added to the solution in the amount of from 0.5 to 10% by weight, preferably 0.1 to 10% by weight.

Typically, the amount of adsorbent particles bonded to the fibre web is in the range of from 0.01 to 0.5 g per gram of web, preferably from 0.1 to 0.5 g/g.

The overall porosity of the filter material of the invention is due to the diameter of the fibre, to the size of the microparticles and to the distribution and the concentration of the microparticles. Then, through the use of the microparticles it is possible to reduce the porosity of the material in order to increase the leukodepletion efficiency of the filter (without the need to drastically modify the original characteristics of the fibres material (e.g. the thickness)) and hence to optimize its final profile.

With the use of the adsorbent particles and particularly of polystyrene-DVB or polyamide particles with a high surface area, the filtering material of the invention also allows to remove low molecular weight substances from blood and blood products such as dyes and photoactive molecules such as viricide-potentiating agents, such as metylene blue, acrydinyl derivatives, psoralen and psoralen derivatives.

EXAMPLE 1

Comparison between a filter made with the new material and a filter made with conventional material.

Whole blood (WB) filters with the new filter material were compared with filters made with conventional filter material.

The filter material according to the invention was made of a non woven web of PBT fibres coated with polyvinylpirrolidone and including bonded polyamide particles having a mean diameter of about 12 µm and with a particle content of about 0.4 g/g of web.

Each filter was made with 30 layers of this new filter material.

The conventional filter material was a non woven web of PBT coated with the same polyvinylpyrrolidone solution used for the new filter material.

WB filters with the conventional filter material were made with 40 layers in one case and with 30 layers in the other one.

Whole blood (range 450-550 ml) was collected from random donors in a PVC bag with 70 ml of CPD. All whole-blood donations were cooled to 20-24° C. under 1,4 butanediol plates. The filtration was performed by gravity.

WBCs in the filtered blood were counted in a Nageotte hemocytometer.

The results obtained are summarised in the following table:

| | Filter | | |
|---|---|---|---|
| | New filter material 30 layers | Conventional filter material 40 layers | Conventional filter material 30 layers |
| WBCs in filtered blood | 80000 ± 70000 | 100000 ± 80000 | 900000 ± 750000 |

These experimental results show that the new filter material has higher efficiency in leukodepletion and it allows to obtain the same results of conventional filters with less material.

EXAMPLE 2

Removal of Acridine Derivatives from RCC

A filter was made with the new filter material as described in example 1 with the use of PS-DVB microspheres in the amount of 0.4 g/g of web.

The mean diameter of microspheres was 35 micron and the surface area was 900 $m^2/g$. Thirty layers of this material were used to make a filter.

An acridine derivatives was added to a bag of RCC with SAG-M (Vol.=ml 270) in order to obtain a concentration of the acridine derivatives of 200 micromol.

The filtration was performed by gravity and the acridine derivatives content after the filtration was less then 1 micromolar.

With a conventional filter (40 layers) there was no removal of the acridine derivatives.

The invention claimed is:

1. A filter device for the depletion of the leukocyte content from blood products comprising:
   a porous element comprising at least one fibrous web having a pore size suitable for leukocyte removal,
   said web comprising fibres of a hydrophobic polymer coated with a hydrophilic polymer suitable to enhance the CWST of said hydrophobic polymer,
   characterised in that said web further includes adsorbent particles having a mean diameter lower than 30 µm, said particles being bonded to said fibres by means of said hydrophilic polymer coating said fibres.

2. The filter device according to claim 1, wherein said web is obtainable by soaking (impregnating) a web of fibres of said hydrophobic polymer with a solution of said hydrophilic polymer including in suspension said adsorbent particles.

3. The filter device according to claim 2, wherein said solution comprises from 0.1 to 10% by wt. of said particles.

4. The filter device according to claim 1, wherein said hydrophilic coating polymer is selected from copolymers obtained by polymerization of vinylacetate and vinylpyrrolidone.

5. The filter device according to claim 1, wherein said absorbent particles are made from a material selected from the group consisting of acrylic polymers, polyesters, polyamides, polyacrylamides, active charcoal and polystyrene-divinylbenzene.

6. The filter device according to claim 1, wherein said hydrophobic polymer is selected from the group consisting of polyethylene, polypropylene, cellulose acetate, polyamides, acrylic polymers, polyacrylonitriles, polyvinylidene fluoride, polyaramides and polyesters, particularly polybutylenterephthalate.

7. The filter device according to claim 1 wherein said web comprises an amount of particles in the range from 0.01 to 0.5 g/g of the fibre web material.

8. The filter device according to claim 1 wherein the hydrophobic polymer is polybutyleneterephthalate and the adsorbent particles are made of polyamide or polystyrene-divinylbenzene polymer and are bonded to the hydrophobic fibres by means of polyvinylpyrrolidone at least partially coating said fibres.

9. The method for removing substances from blood products comprising feeding said blood products through a filter according to claim 1.

10. The blood purification device comprising a filter according to claim 1.

11. The blood purification device according to claim 10 consisting of blood bag device for the separation of blood into leukocyte depleted blood components, comprising a first bag connected, in fluid flow communication, with a second bag through said filter.

* * * * *